(12) United States Patent
Barrett

(10) Patent No.: US 7,744,647 B2
(45) Date of Patent: Jun. 29, 2010

(54) INTRAOCULAR LENS

(76) Inventor: Graham David Barrett, 56 Dampier Avenue, Western Australia, City Beach (AU) 6015

( * ) Notice: Subject to any disclaimer, the term of this patent is extended or adjusted under 35 U.S.C. 154(b) by 109 days.

(21) Appl. No.: 10/546,141

(22) PCT Filed: Feb. 20, 2004

(86) PCT No.: PCT/AU2004/000200

§ 371 (c)(1),
(2), (4) Date: Aug. 18, 2005

(87) PCT Pub. No.: WO2004/073558

PCT Pub. Date: Sep. 2, 2004

(65) Prior Publication Data

US 2007/0010882 A1    Jan. 11, 2007

(30) Foreign Application Priority Data

Feb. 21, 2003    (AU) .............................. 2003900952

(51) Int. Cl.
*A61F 2/16*    (2006.01)

(52) U.S. Cl. ................................................... 623/6.37
(58) Field of Classification Search ................ 623/6.11, 623/6.37–6.4, 6.43
See application file for complete search history.

(56) References Cited

U.S. PATENT DOCUMENTS 6,197,059 B1 *   3/2001   Cumming .................. 623/6.39
6,387,126 B1     5/2002   Cumming

FOREIGN PATENT DOCUMENTS

| WO | WO 00/01323 | 1/2000 |
| WO | WO 00/35379 | 6/2000 |
| WO | WO 01/81075 A2 | 11/2001 |
| WO | WO 2004/004606 A2 | 1/2004 |

* cited by examiner

*Primary Examiner*—William H Matthews
(74) *Attorney, Agent, or Firm*—Pearne & Gordon LLP

(57) ABSTRACT

Intraocular lens implant (10) for providing accommodation for near vision includes an optic (20) centrally disposed in a flexible membrane (30) and at least one haptic (40) outwardly extending from the flexible membrane. The flexible membrane is adapted in use to facilitate translatable movement of the optic in response to attempted accommodation by the ocular substrate.

6 Claims, 2 Drawing Sheets

INTRAOCULAR LENS

FIELD OF THE INVENTION

The present invention relates to an intraocular lens implant for providing accommodation for near vision, in particular to an intraocular lens implant that provides for anterior translation of the optic upon contraction of the ciliary muscles.

BACKGROUND OF THE INVENTION

The human eye has two major refracting elements responsible for focusing light on the retina The cornea is the anterior refracting surface responsible for the majority of the focusing power of the eye equivalent to approximately 43 diopters whilst the remaining power of approximately 19 diopters is from the crystalline lens which is a transparent structure that focuses light in the human eye.

Emmetropia refers to a state of focus of the human eye where objects viewed at a distance are in focus on the retina. If axial length of the eye is such that the focal point is in front of the retina the refractive error is known as myopia and if the focal point is beyond the retina the refractive error is termed hypermetropia If the focus of the eye is unequal in different meridians the refractive error is known as astigmatism that can be associated with myopia or hypermetropia.

The power of the cornea is a fixed quantity and the ability to maintain focus for objects closer than infinity depends on altering the focus of the crystalline lens.

The human lens is attached to the wall of the eye by fine filamentary fibers known as zonules that attach the equatorial region of the lens to the region of the eye wall surrounded by a circular muscle known as the ciliary muscle. In an emmetropic individual, when an object in the distance is viewed the ciliary muscle is relaxed and the zonules are under tension. The elastic capsule of the lens is taut and the curvature of the lens is influenced and slightly flattened by these forces. If the object of regard is changed to a near object a reflex stimulates contraction of the ciliary body which relaxes the zonular attachments to the lens. This allows the elastic capsule of the lens and the malleable lens fibers to assume a more spherical shape and due to the increase in pressure in the posterior segment the lens moves forward. Both factors increase the focusing power of the lens by the required amount so that the near object of regard remains in focus. This process is referred to as accommodation.

Up to the $4^{th}$ decade the human crystalline lens is capable of altering its focus to maintain clarity of vision for near objects by the process of accommodation but this power is gradually lost over the next two decades. This is thought to occur due to several factors including an increased rigidity of the lens fibers, an increase in the diameter of the lens, and possible reduced elasticity of the capsule and zonules. The refractive error describing this inability to achieve near focus is known as presbyopia and is the reason for the progressive need for reading glasses for individuals from the $5^{th}$ decade of life.

Spectacles or contact lenses placed in the optical pathway can correct the focus for clarity of vision in patients with myopia, hypermetropia, or astigmatism. The correction of presbyopia includes separate glasses for reading, bifocal or multifocal spectacles. Simultaneous near and distant vision can be achieved by multifocal contact lenses that provide simultaneous foci for near and distance. This method however is associated with reduced contrast in vision that may be disturbing to many patients.

More recently it has been found that laser surgery can alter the corneal curvature to correct refractive errors such as myopia, hypermetropia or astigmatism. Phakic intraocular lenses can be placed in the anterior chamber of the eye or behind the iris to correct myopia or hyperopia and the lens can be removed and replaced by an intraocular lens implant for the purpose of correcting a refractive error.

Surgical procedures have also been proposed to restore accommodation in the presbyopic age group. These include sclera implants to expand the diameter of the globe to counteract the expansion of the crystalline lens that occurs with age. Radial incisions at the limbus have also been considered for the same purpose. These procedures however have not proved to be sufficiently reliable or predictable. Laser procedures can alter the corneal curvature to produce a multifocal refracting surface. Corneal implants placed in the corneal stroma can also produce a similar bifocal or multifocal refraction. Finally intraocular lenses with a diffractive or refractive surface can be constructed to provide multiple foci and allow simultaneous focus for distance and near vision. These lenses can be implanted after surgical removal of the crystalline lens or placed in front of the crystalline lens as a phakic implant. Unfortunately all surgical procedures which depend on simultaneous near and distance vision are compromised by reduced contrast and are often associated with undesirable effects such as haloes around lights which may be disturbing to individual patients. The development of an intraocular lens capable of accommodation similar to the crystalline lens in a young individual is therefore extremely desirable.

Opacification of the lens known as cataract formation is a common cause of poor vision in the elderly and can be corrected surgically. Modern cataract surgery is performed by manual extracapsular cataract extraction or by phacoemulsification. Manual extracapsular cataract extraction involves expressing the hard nucleus of the cataract through a 10 mm to 12 mm incision. Phacoemulsification utilises ultrasonic energy transmitted by a needle to fragment the nucleus and allow aspiration of the cataract through a 2.5 mm to 3.2 mm incision. A small incision is desirable in cataract surgery to avoid distortion of the corneal curvature known as astigmatism. In both operations an opening is made in the anterior capsule to allow removal of the lens contents. The capsular bag remnant, however, is left in situ to provide support for an intraocular lens implant which is inserted following removal of the cataract to replace the focusing power of the natural crystalline lens. It is known to provide an intraocular lens implant to replace the cataractous or clear crystalline lens. The power of the lens can be accurately selected prior to surgery so that the patient is emmetropic i.e. clear focus is achieved for objects in the distance. An intraocular lens implant typically comprises a centre focusing element, known as the optic and a peripheral support structure known as the haptic. The haptic of an intraocular lens is the outwardly extending supporting element which interacts with the anterior and posterior leaflets of the capsular bag remnant to ensure fixation and stability. The optic and the haptic of the intraocular lens may be manufactured from transparent rigid plastics material such as polymethyl methacrylate or from flexible plastic materials such as acrylic, silicone or hydrogel polymers. Intraocular lens implants manufactured from flexible materials are preferable to those made of rigid materials because the lens may be folded to allow insertion through a small incision in the sclera or outercoat of the eye and is then allowed to unfold to its original dimensions.

The optic and haptic of the intraocular lens may be manufactured from the same material as a single piece unit or the haptic may be attached to the optic by a variety of mechanisms. There may be one or a plurality of haptics attached to the optic, although the most common configuration includes an optic with two outwardly extending diametrically opposed haptics. The purpose of the haptic is to provide optimal centration of the optic as well as a means of fixation of the implant within a capsular bag remnant of the original lens following cataract or lens extraction. It is preferable that the haptics conform to the periphery of the capsular bag to provide a larger surface area of contact between the intraocular lens implant and the capsular bag and to ensure centration of the optic.

It is also possible to implant a lens in front of the anterior capsule behind the iris with the haptics resting in the region between the root of the iris and ciliary processes, known as the ciliary sulcus. As previously mentioned intraocular lenses may also be inserted in phakic eyes to correct refractive errors, such as myopia or hyperopia. In these circumstances the intraocular lens implant may be placed in front of the crystalline lens behind the iris with the haptic providing support in the ciliary sulcus. Furthermore, as an alternative site of implantation in phakic eyes, intraocular lenses may be inserted in front of the iris in the anterior chamber with the haptics resting in the angle of the anterior chamber.

In all these instances it is preferable that the haptics conform to the periphery of the capsular bag or to the ciliary sulcus or the angle of the anterior chamber in the phakic eye The prior art discloses several haptic designs, including a flange style or loop style, which seek to maximise the surface areas of contact between the intraocular lens implant and the capsular bag. The most common design includes two loop style haptics attached at diametrically opposed points of an optic wherein terminal ends of the haptics extend arcuately towards the periphery of the capsular bag.

The fixation and stability of the intraocular lens implant is not solely dependent on the rigidity of the supporting haptics of an intraocular lens, but is also dependent on fusion of leaflets of anterior and posterior capsule in the interval between the optic of the implant and the terminal of the haptic in contact with the periphery of the capsular bag. It is preferable to maintain as large an interval as possible to provide maximum opportunity for fusion to occur.

Post-operative shrinkage of the capsular bag is not an unusual occurrence. The aforementioned interval may be maintained by a rigid haptic which resists shrinkage of the capsular bag, or by a design for haptics manufactured from flexible plastics which maintains an interval between the terminal of the haptic and the optic in the even of shrinkage of the capsular bag. In order that the design should accommodate the various sizes of capsular bag that will be encountered in different individuals as well as the varying degrees of shrinkage that would occur during the post-operative phase, it is preferable that the haptics should be compressible.

A distinct disadvantage however, of the current haptic designs is that the haptic terminal may be flexed at any point between the haptic terminal and the haptic optic junction towards the optic such that the interval between the haptic terminal and the optic is reduced to the extent where migratory fusion of the leaflets of the anterior and posterior capsule fails to occur. The Author has described (International Publication Number WO00/01323) a haptic design which maintains an interval between the terminal haptic and the optic and provides better conformity of the terminal portion of the haptic with the periphery of the capsular bag.

Previous descriptions of intraocular lenses capable of an accommodative effect include lenses constructed to have an induced increase in curvature of the optic of the lens or a change in position of the lens during attempted focus for near objects. The latter include lenses with a haptic constructed with a hinge to allow forward translation of the optic with attempted accommodation. This occurs due to the increase in pressure in the vitreous or liquid in the posterior segment of the globe induced by contraction of the ciliary body. The accommodative effect of this type of intraocular lens however varies widely in individual patients. The unpredictable results of a intraocular lens with a hinged haptic are due to the differences in fixation that occur with an implant placed in the capsular bag after cataract surgery or removal of the normal crystalline lens by similar techniques. The amount of overlap of the anterior capsular bag leaflets over the haptic and edge of the optic is variable as is the extent and area of fusion of the anterior capsular leaflets to the posterior capsule. This variability interferes with the ability of the hinged haptic to allow forward movement of the optic in response to contraction of the ciliary body in attempted accommodation and is an important factor in the unpredictable accommodative effect that has been encountered in present day accommodative intraocular implants.

The present invention attempts to overcome at least in part some of the aforementioned disadvantages.

SUMMARY OF THE INVENTION

In accordance with a first aspect of the present invention there is provided an intraocular lens implant for providing accommodation for near vision comprising an optic substantially centrally disposed in a flexible membrane and at least one haptic outwardly extending from the flexible membrane to fixate the intraocular lens implant in an optical substrate, wherein the flexible membrane is adapted in use to facilitate translatable movement of the optic in response to attempted accommodation by the ocular substrate.

BRIEF DESCRIPTION OF THE DRAWINGS

The present invention will now be described, by way of example, with reference to the accompanying drawings, in which.

DETAILED DESCRIPTION OF AN EMBODIMENT OF THE INVENTION

Referring to the Figures, wherein like numerals and symbols refer to like parts throughout, there is shown an intraocular lens implant 10, including an optic 20 disposed in a flexible membrane 30, and a pair of diametrically disposed haptics 40 outwardly extending from the flexible membrane 30.

The optic 20 is a substantially circular convex member and may be manufactured from a transparent rigid plastics material such as polymethyl methacrylate, or preferably from a flexible plastics material, such as acrylic, silicone or suitable hydrogels, which would allow the optic 20 to be folded and inserted through a small. incision in the sclera or outercoat of the eye, whereupon the optic 20 reverts to its original shape once implanted in vivo.

The optic 20 may be equi-convex, asymmetrical bi-convex with its steeper radius placed anteriorally, or plano-convex. Preferably the optic 20 is about 5.0 mm in diameter.

Figure 1:
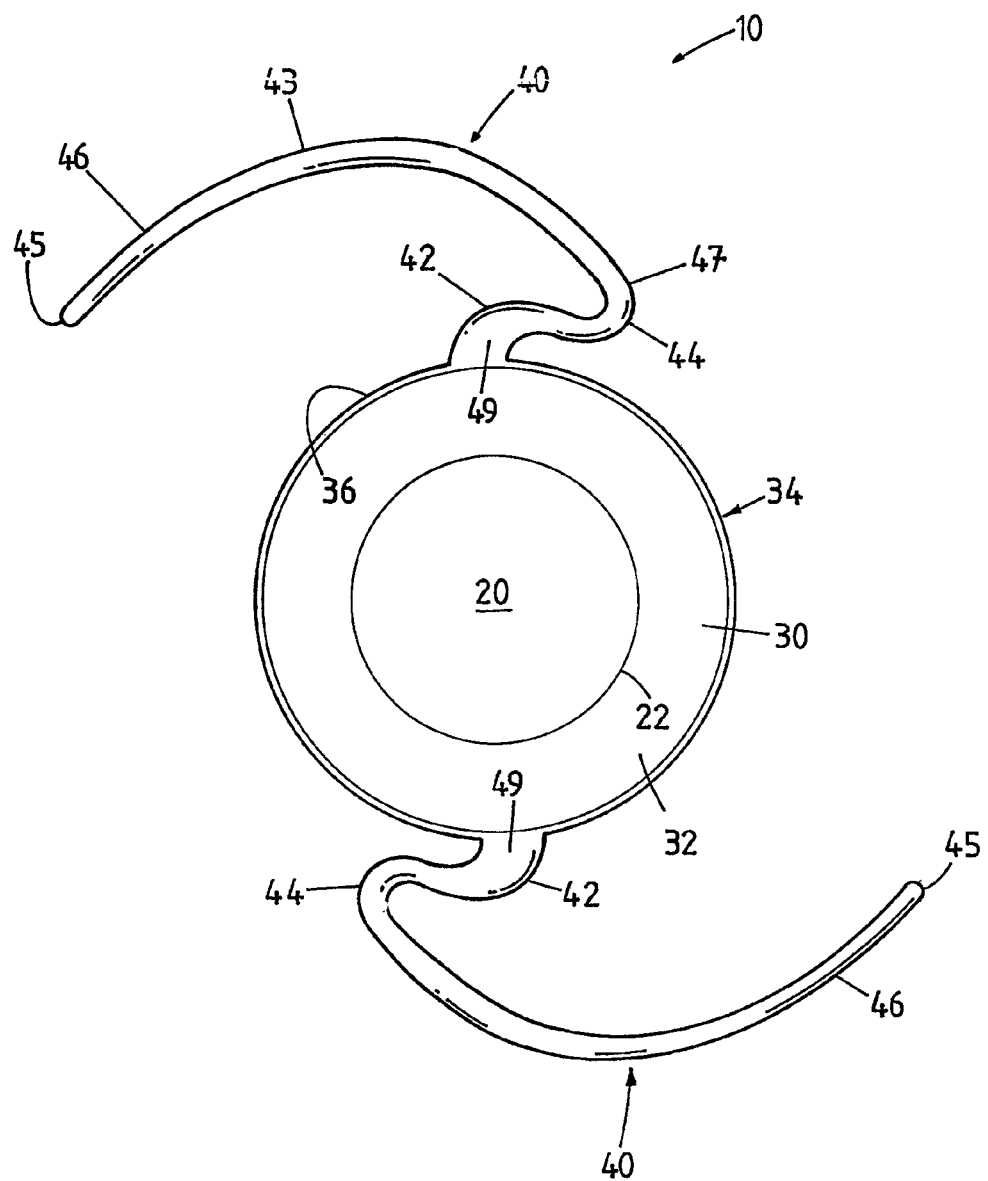
FIG. 1 is a plan view of an intraocular lens implant in accordance with the present invention.
Figure 5:
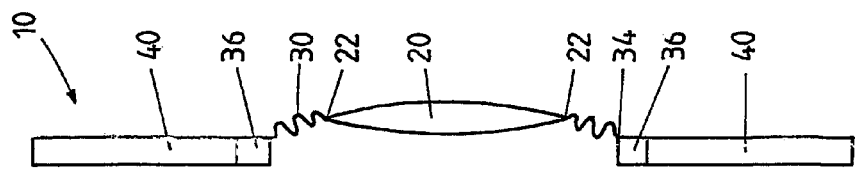
FIG. 5 is a side view of a further alternative embodiment of the intraocular lens implant in accordance with the present invention.

The optic 20 is substantially centrally disposed in the flexible membrane 30 such that the optic 20 is surrounded by an annulus 32 of flexible membrane 30 of about 0.05 mm to 0.5 mm in width depending on the mechanical properties of the plastics material from which the flexible member 30 formed. The annulus 32 of flexible membrane 30 laterally extends from a circumferential periphery 22 of the optic 20. The flexible membrane 30 may also have a concertinaed appearance, as shown in FIG. 5, such that it may be resiliently stretched, thereby facilitating anterior and posterior translation of the optic 20. Typically, the flexible membrane 30 is also elastic.

Figure 2:
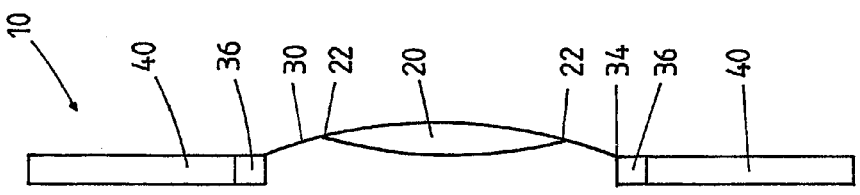
FIG. 2 is a first side view of the intraocular lens implant shown in FIG. 1 in a first position.
Figure 3:
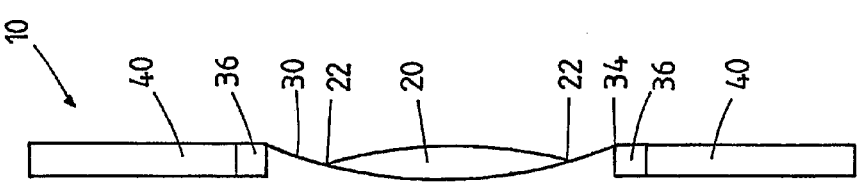
FIG. 3 is a second side view of the intraocular lens implant shown in FIGS. 1 and 2 in a second position.

When the ocular substrate attempts accommodation, the ciliary muscles contract and the flexible and resilient character of the flexible membrane 30 facilitates forward translation of the optic 20 from a first posterior position as shown in FIG. 2 to a second anterior position as shown in FIG. 3. To a certain extent, the degree of anterior translation of the optic 20 of the present invention will be dependent on the width of the flexible membrane 30, the elasticity of the flexible membrane 30, or the extent to which the concertinaed flexible membrane 30 can be resiliently stretched in response to pressure exerted by the vitreous or liquid in the posterior segment of the ocular substrate on the flexible membrane 30 induced by contraction of the ciliary muscles during accommodation.

An outermost peripheral edge 34 of the flexible membrane 30 is provided with a substantially annular relatively rigid rim 36. In the instance where the intraocular lens implant 10 is arranged to be folded and inserted through a small incision, the rim 36 should be sufficiently flexible and resilient to allow folding thereof and then resumption of its original shape once implanted in vivo.

Figure 4:
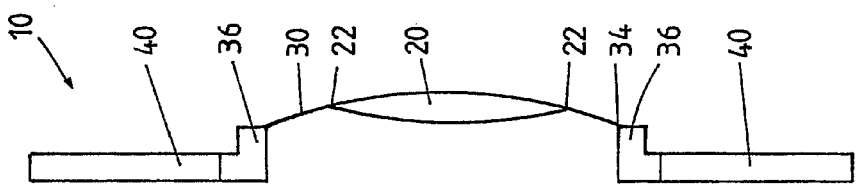
FIG. 4 is a side view of an alternative embodiment of the intraocular lens implant in accordance with the present invention.

It will be understood that a cross-section of the annular rim 36 may be circular, quadrangular as shown in FIGS. 2 and 3, or fluted. Further, with reference to FIG. 4, the cross-section of the rim 36 may be L-shaped with a base portion of the cross-section disposed rearwardly of an upright portion of the L-shaped rim. Preferably, the outermost edge 34 of the flexible membrane 30 is disposed rearward most of the rim 36, as posteriorally as possible in order for the optic 20 and membrane 30 to remain closely in contact with the capsular bag remnant.

In a preferred embodiment of the intraocular lens implant 10, each haptic 40 includes a first portion 42 interconnected to a second portion 46 by an elbow-shaped bend 44. An end of the first portion 42 remote from the bend member 44 of the haptic 40 is attached to the annular rim 36 of the flexible membrane 30 at a haptic-membrane junction 49. The first portion 42 of each haptic 40 extends outwardly from the annular rim 36 in an arcuate manner in a clockwise direction.

The second portion 46 of the haptic 40 extends outwardly from the elbow-shaped bend 44 in an arcuate manner in an anticlockwise direction. In other embodiments of the invention it will be appreciated that, alternatively, the first portion 42 could extend outwardly from the annular rim 36 in an arcuate manner in an anti-clockwise direction and the second portion 46 could extend outwardly from the elbow-shaped bend 44 in an arcuate manner in a clockwise direction. A free end of the second portion 46 of the haptic 40 comprises a haptic terminal 45 of the haptic 40.

The haptics 40 may be manufactured from polymethyl methacrylate, or preferably from flexible plastic materials such as acrylic, silicone or hydrogels.

Preferably the first portion 42 of the haptics 40 are attached to the annular rim 36 at respective diametrically opposed locations. In other words, the haptic-membrane junctions 49 are spaced equiangularly around annular rim 36.

In use, the haptics 40 facilitates optimal conformation of the respective haptic terminals 45 with a capsular bag by providing two counterbalanced points 43, 47 for flexion to occur when the haptics 40 are compressed by post-operative shrinkage of the capsular bag. This is achieved by the haptic 40, whose first portion 42 extends outwardly from the annular rim 36 of the flexible membrane 30 in an arcuate manner and whose second portion 46 reverses direction such that the elbow 44 is disposed on the opposite side of the haptic-membrane junction 49 to the peripheral area of the contact of the haptic terminal 45 with the capsular bag.

Compression of the second portion 46 of the haptic 40 at a flexion point 43 distal to the elbow-shaped bend 44 will tend to incline the haptic terminal 45 of the haptic 40 towards the optic 20 and the flexible membrane 30, thereby decreasing the interval between the optic 20 and the flexible membrane 30 of the implant and the haptic terminal 45 of the haptic 40 in contact with the periphery of the capsular bag. This tendency is counterbalanced in the present invention where compression of the second portion 46 of the haptic 40 at the flexion point 47 proximal to the elbow-shaped bend 44 will tend to decrease the interval between the optic 20 and the flexible membrane 30 of the implant and the elbow-shaped bend 44 of the haptic 40 resulting in an expansion of the peripheral are of the second portion 46 of the haptic, thereby increasing the interval between the optic 20 and the flexible membrane 30 of the implant and the terminal 45 of the haptic 40 in contact with the periphery of the capsular bag.

It is considered within the scope of the invention if one or a plurality of haptics 40 are attached to the rim 36 of the flexible membrane 30 and the terminals 45 of the haptics 40 extend in identical or opposite directions. It will also be understood that alternative haptics 40, other than those described, are deemed within the scope of the present invention.

When the ocular substrate attempts accommodation, the ciliary muscles contract and the flexible and resilient character of the flexible elastic membrane 30 facilitates forward translation of the optic 20 from a first position as shown in FIG. 2 to a second position as shown in FIG. 3. The flexible membrane 30 facilitates anterior and posterior translation of the optic 20 in response to pressure exerted by the vitreous or liquid in the posterior segment of the ocular substrate on the flexible membrane 30 induced by contraction and relaxation of the ciliary muscles during accommodation. The magnitude of the anterior translation is determined by either the degree of pressure applied to the surface area of the capsular bag containing the intraocular lens implant 10 and/or the size of the surface area to which pressure is applied.

Typically, in prior art systems, such as the intraocular lens with the hinged haptic as described previously, the entire surface area of the capsular bag containing the intraocular implant has a diameter of about 10.5 mm which affords a surface area of about 86.59 mm$^2$. By contrast, the portion of the capsular bag acting on the optic 20 and the flexible membrane 30 of the intraocular lens 10 of the present invention is about 6 mm in diameter which affords a surface area of about 28.27 mm$^2$. The difference in size of surface area subjected to the same pressure accounts for about a three-fold increase in forward translation of the optic 20 of the present invention, compared to other prior art systems, which enhances its magnification. Increased translation is particularly advantageous as it is estimated that a 1 mm of forward translation for an intraocular lens implant is sufficient to provide approximately 2 diopters of additional effective power depending on the optic power of the optic.

The increase in anterior translation of the optic 20 observed with the present invention in comparison with prior art systems is readily illustrated by the following formulae: Let Volume $V_1 = a_1 x_1$ where $V_1$ is the volume of vitreous fluid acting on the prior art capsular bag-intraocular lens implant complex; $a_1$ is the surface area of the prior art capsular bag-intraocular lens implant complex; and $x_1$ is the anterior translation of the prior art capsular bag-intraocular lens implant complex.

Let Volume $V_2 = a_2 x_2$ where $V_2$ is the volume of vitreous fluid acting on the optic 20 and the flexible membrane 30 of the present invention; $a_2$ is the surface area of the optic 20 and the flexible membrane 30 of the present invention; and $x_2$ is the anterior translation of the optic 20 and the flexible membrane 30 of the present invention.

Let $V_1 = V_2$ since the volume of vitreous fluid is the same in each case, and $a_2 < a_1$ since the surface area of the optic 20 and the flexible membrane 30 of the present invention is less than the surface area of the prior art capsular bag-intraocular lens implant complex.

$P_1 V_1 = nRT$ at any given temperature T, where $P_1$ is the pressure exerted by the vitreous fluid on the prior art capsular bag-intraocular lens implant complex. $P_2 V_2 = nRT$ at any given temperature T, where $P_2$ is the pressure exerted by the vitreous fluid on the optic 20 and the flexible membrane 30 of the present invention.

Let $P_1 = P_2$
$P_1 = nRT \ V_1 = nRT \ a_1 x_1$
$P_2 = nRT \ V_2 = nRT \ a_2 x_2$
$nRT \ a_1 x_1 = nRT \ a_2 x_2$
If $a_2 < a_1$ then $x_2 > x_1$.

In this particular embodiment, the haptics 40 attached to the membrane 30 are encapsulated by the anterior and posterior leaflets of the capsular bag remnant to ensure fixation and stability, thereby rendering the haptics 40 substantially rigid and immobile even in response to contraction and relaxation of the ciliary muscles upon attempted accommodation. In contrast to the prior art, particularly the intraocular lens implant reliant on hinged haptics as described by Cumming in U.S. Pat. No. 6,494,911, anterior translation of the optic 20 of the intraocular implant 10 of the present invention is not reliant on the mobility of the haptic or its flexibility. Whereas the accommodative effect in a prior art lens implant relies on the forward or anterior translation of the capsular bag-intraocular lens implant complex, anterior translatory movement is only facilitated for the optic 20 and the flexible membrane 30, since the peripheral area of the implant 10 comprising the haptics 40 is stable. The concept of using a flexible membrane 30 to facilitate anterior translation of only the optic 20, leaving the haptics 40 fixed to the ocular substrate appears to be unique in comparison to the prior art.

Modifications and variations as would be apparent to a skilled addressee are deemed to be within the scope of the present invention.

The invention claimed is:

1. An intraocular lens for providing accommodation for near vision in a human eye having an optical axis comprising an optic having a periphery, a flexible, elastic membrane in the form of an annulus extending entirely around the periphery of the optic and thus surrounding the optic such that the optic is substantially centrally disposed in said flexible membrane, the flexible membrane having an outer diameter of about 5.1 - 6 mm and an outermost peripheral edge, a relatively rigid annular rim being connected to the outermost peripheral edge of the flexible membrane and surrounding the flexible membrane in its entirety, at least one haptic having a proximal end and a distal end outwardly extending from the annular rim of the flexible membrane to fixate the intraocular lens implant in an optical substrate of the eye, the proximal end of the or each haptic being attached to the annular rim at a haptic membrane junction, the or each haptic extending outwardly away from the annular rim in an arcuate manner, the distal end of the or each haptic having a terminal portion comprising a free end spaced from the annular rim, the arrangement being such that there is an interval between the annular rim of the flexible membrane and the terminal portion, the or each haptic being arranged to contact a capsular bag or wall of an eye to be encapsulated in the interval between the annular rim of the flexible membrane and the terminal portion by fusion of anterior and posterior leaflets of a capsular bag remnant in the ocular substrate ensure fixation and stability of the or each haptic thereto, thereby rendering the or each haptic and the annular rim substantially rigid and immobile to translatory movement along the optical axis in response to contraction and relaxation of ciliary muscles upon attempted accommodation of the ocular substrate, wherein the flexible, elastic membrane is configured to facilitate anterior and posterior translatable movement of the optic in response to attempted accommodation by the ocular substrate of the eye, wherein the accommodation forces are transmitted to an effective implant diameter of about 5.1 - 6 mm thereby providing about a three fold increase in translation compared to an implant having non fixed haptics.

2. The intraocular lens implant according to claim 1, wherein an annulus of flexible membrane laterally extends from a circumferential periphery of the optic.

3. The intraocular lens implant according to claim 1, wherein the flexible membrane is resilient.

4. The intraocular lens implant according to claim 1, wherein the flexible membrane is concertinaed.

5. The intraocular lens implant according to claim 1, wherein a cross-section of the annular rim is circular, quadrangular, fluted, or L-shaped.

6. The intraocular lens implant according to claim 1, wherein an outermost edge of the flexible membrane is disposed rearwardmost of the annular rim.

* * * * *

UNITED STATES PATENT AND TRADEMARK OFFICE
CERTIFICATE OF CORRECTION

PATENT NO. : 7,744,647 B2  Page 1 of 1
APPLICATION NO. : 10/546141
DATED : June 29, 2010
INVENTOR(S) : Graham David Barrett It is certified that error appears in the above-identified patent and that said Letters Patent is hereby corrected as shown below:

Column 5, line 1, replace the word "small." with -- small --

Column 6, line 31, replace the word "are" with -- arc --

Signed and Sealed this

Twenty-first Day of September, 2010

David J. Kappos
*Director of the United States Patent and Trademark Office*